United States Patent
Meng et al.

(10) Patent No.: US 11,987,024 B2
(45) Date of Patent: May 21, 2024

(54) MULTILAYER TUBING HAVING INTERMEDIATE LAYER WITH ADDITIVES

(71) Applicant: CareFusion 303, Inc., San Diego, CA (US)

(72) Inventors: Fanqing Meng, Buffalo Grove, IL (US); Marc William Weimer, South Jordan, UT (US)

(73) Assignee: CAREFUSION 303, INC., San Diego, CA (US)

( * ) Notice: Subject to any disclaimer, the term of this patent is extended or adjusted under 35 U.S.C. 154(b) by 386 days.

(21) Appl. No.: 17/033,511

(22) Filed: Sep. 25, 2020

(65) Prior Publication Data

US 2022/0099223 A1 Mar. 31, 2022

(51) Int. Cl.
*B32B 27/08* (2006.01)
*A61L 29/04* (2006.01)
(Continued)

(52) U.S. Cl.
CPC ............ *B32B 27/08* (2013.01); *A61L 29/041* (2013.01); *A61L 29/14* (2013.01); *A61M 5/14* (2013.01);
(Continued)

(58) Field of Classification Search
CPC ........... B32B 1/08; B32B 27/16; B32B 27/18; B32B 27/20; B32B 27/22; B32B 27/30; B32B 27/302; B32B 27/304; B32B 27/32; B32B 27/327; B32B 27/36; B32B 2250/03; B32B 2250/04; B32B 2250/242; B32B 2250/244; B32B 2250/246; B32B 2250/248; B32B 2264/10; B32B 2264/102; B32B 2264/1022; B32B 2264/105; B32B 2264/12; B32B 2270/00; B32B 2307/4026; B32B 2307/41; B32B 2307/412;
(Continued)

(56) References Cited

U.S. PATENT DOCUMENTS 4,303,457 A * 12/1981 Johansen ................ B29C 48/09
156/149
4,469,483 A * 9/1984 Becker .............. A61M 25/0108
128/DIG. 21
(Continued)

FOREIGN PATENT DOCUMENTS

DE 3204762 A1 8/1983
EP 1710482 A1 10/2006
(Continued)

OTHER PUBLICATIONS

CODAN LightSafe, downloaded from https://www.codanusa.com/Innovations-Solutions/CODAN-LightSafe on Dec. 22, 2020, 3 pages.
(Continued)

*Primary Examiner* — James C Yager
(74) *Attorney, Agent, or Firm* — Morgan, Lewis & Bockius LLP

(57) ABSTRACT

Tubing, such as medical tubing for administration of intravenous fluid, can include an inner layer, an outer layer concentrically disposed about and surrounding the inner layer, and an intermediate layer interposed between the inner and outer layers. The intermediate layer may include a light protection additive therein.

18 Claims, 1 Drawing Sheet

(51) Int. Cl.

| | |
|---|---|
| *A61L 29/14* | (2006.01) |
| *A61M 5/14* | (2006.01) |
| *A61M 25/00* | (2006.01) |
| *A61M 25/01* | (2006.01) |
| *B29C 48/09* | (2019.01) |
| *B29C 48/21* | (2019.01) |
| *F16L 11/12* | (2006.01) |
| *B29K 105/00* | (2006.01) |
| *B29L 23/00* | (2006.01) |

(52) U.S. Cl.
CPC .... *A61M 25/0009* (2013.01); *A61M 25/0043* (2013.01); *A61M 25/0108* (2013.01); *B29C 48/09* (2019.02); *B29C 48/21* (2019.02); *F16L 11/12* (2013.01); *B29K 2105/0005* (2013.01); *B29K 2995/0055* (2013.01); *B29L 2023/007* (2013.01)

(58) Field of Classification Search
CPC ............ B32B 2307/42; B32B 2307/51; B32B 2307/71; B32B 2307/714; B32B 2307/732; B32B 2535/00; B32B 2597/00; B32B 3/08; B32B 7/023; B32B 25/042; B32B 25/16; B32B 25/20; B32B 27/08; B32B 27/285; B32B 27/40; F16L 11/00; F16L 11/04; F16L 11/10; F16L 11/12; F16L 11/14; B29C 48/00; B29C 48/16; B29C 48/21; A61M 25/0009; A61M 25/0012; A61M 25/0043; A61M 25/0045; A61M 25/0108; A61M 5/14; A61M 39/08; A61M 2025/0008; A61L 29/041; A61L 29/14; B29K 2105/0005; B29K 2995/0055; B29L 2023/007
See application file for complete search history.

(56) References Cited

U.S. PATENT DOCUMENTS

| | | | |
|---|---|---|---|
| 4,627,844 A | 12/1986 | Schmitt | |
| 4,657,024 A | 4/1987 | Coneys | |
| 4,707,389 A | 11/1987 | Ward | |
| 5,356,709 A | 10/1994 | Woo et al. | |
| 6,007,520 A * | 12/1999 | Sudo | A61L 29/06 428/494 |
| 6,149,997 A | 11/2000 | Patel et al. | |
| 2002/0010386 A1* | 1/2002 | Matsushita | B32B 27/08 600/140 |
| 2006/0178485 A1* | 8/2006 | Shimakage | C08F 8/04 525/242 |
| 2013/0116113 A1* | 5/2013 | Kaita | C08F 222/26 526/281 |
| 2014/0205778 A1* | 7/2014 | Sakai | C08K 5/0016 428/36.9 |
| 2016/0175128 A1* | 6/2016 | Diaz | A61F 2/954 623/1.11 |
| 2018/0080586 A1 | 3/2018 | Berger et al. | |

FOREIGN PATENT DOCUMENTS

| | | |
|---|---|---|
| WO | WO-2019103081 A1 | 5/2019 |
| WO | WO-2019142808 A1 | 7/2019 |

OTHER PUBLICATIONS

Leonard, "Peeling Back the Layers of Coextruded Medical Tubing," Apr. 11, 2012, downloaded from https://www.mddionline.com/peeling-back-layers-coextruded-medical-tubing, 6 pages.

Cohen, et al., Near-UV Reflective Structural Color Via Layer-by-Layer Deposition, retrieved from https://tlo.mit.edu/technologies/near-uv-reflective-structural-color-layer-layer-deposition, on Dec. 22, 2020, 4 pages.

International Search Report and Written Opinion for Application No. PCT/US2021/051362, dated Jan. 5, 2022, 14 pages.

\* cited by examiner

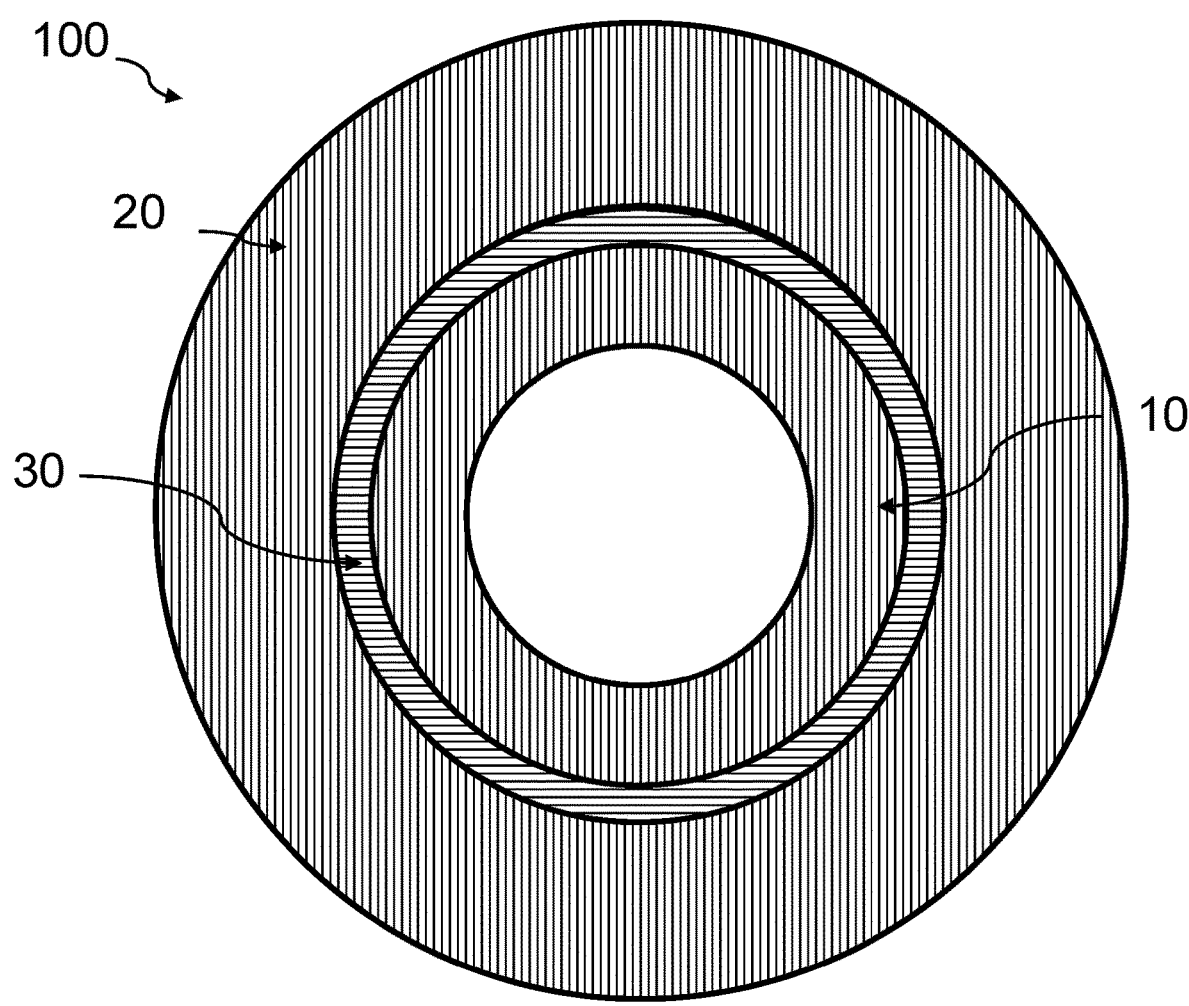

MULTILAYER TUBING HAVING INTERMEDIATE LAYER WITH ADDITIVES

TECHNICAL FIELD

The present disclosure generally relates to tubing and, in particular, to medical tubing for administration of medical fluid by infusion.

BACKGROUND

Plastic tubing is extensively used in the medical field, particularly for patient analysis and treatment procedures. However, different and sometimes incompatible demands are required for medical tubing. For example, medical tubing should be inert and avoid contamination of fluid transported therethrough. But many plastic materials that have such characteristics tend to be inflexible. In many applications, however, medical tubing is pinched or clamped or used with infusion pumps that move fluid through the tubing by compressing the tubing. Such uses require the tubing to be flexible.

To address the differing demands placed on medical tubing, such tubing has been made with multiple layers of differing polymeric materials or with additives such as plasticizers to change the characteristics of the tubing. However, multiple layered tubing made of different materials can suffer from delamination and thus sometimes include adhesive "tie layers" between incompatible materials. In addition, tubing made with additives have the potential of migration and contamination of the additive into fluid transported therethrough. Further, plasticized polymeric materials such as plasticized polyvinyl chloride can be sticky and leads to occlusion and tearing of the tubing.

SUMMARY

In view of the challenges described above, a continuing need exists for medical tubing that can address differing demands of medical applications.

In accordance with various embodiments of the present disclosure, tubing, such as medical tubing for administration of intravenous fluid may include an inner layer, an outer layer concentrically disposed about and surrounding the inner layer, and an intermediate layer interposed between the inner and outer layers. The intermediate layer may include a light protection additive therein.

In accordance with various embodiments of the present disclosure, a method of forming a multi-layer tubing may include co-extruding a base polymeric resin material into an inner layer, an outer layer, and an intermediate layer of the multi-layer tubing. The intermediate layer may include a light protection additive having a predetermined concentration.

Additional advantages of the subject technology will become readily apparent to those skilled in this art from the following detailed description, wherein only certain aspects of the subject technology are shown and described, simply by way of illustration. As will be realized, the subject technology is capable of other and different configurations, and its several details are capable of modifications in various other respects, all without departing from the subject technology. Accordingly, the drawings and description are to be regarded as illustrative in nature, and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 1 illustrates a cross-section of a three-layer tubing in accordance with an aspect of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Aspects of the subject technology relate to tubing and, in particular, to medical tubing for administration of medical fluid by infusion. Various aspects of the present disclosure provide a medical grade tubing having a sandwiched three-layer structure including an inner layer, an outer layer, and an intermediate layer interposed between and joined to the inner and outer layer resin materials. In some embodiments, the inner, outer, and intermediate layers may be formed from a same base polymeric resin material. This configuration where the inner, outer, and intermediate layers may be formed from a same base polymeric resin material advantageously obviates the need for a tie layer which is conventionally needed to maintain the bond between the multiple layers and prevent delamination of the multiple layers of the tubing. For example, because the same compatible base resin with the same polarity and chemical composition is used in each of the three layers, it is not necessary to have a tie layer in between to keep the inner, outer, and intermediate layers of the tubing from delaminating.

Medical tubing can include various additives and/or colorants. For example, medical tubing for delivering drug and nutrition to patients generally needs to fulfil requirements necessary clinic applications, for instance, light protection capability in the range of 250 to 450 nm with a minimum 90% blockage to protect light-sensitive medical fluids flowing in the tubing. Colorants can also be included with medical tubing as an identifier of a particular clinical use.

According to various embodiments of the present disclosure, light protection additives and/or colorants may be incorporated into the carrier resin of the intermediate layer. The light protection additives may advantageously provide the above referenced light protection capability range to protect light-sensitive medical fluids flowing in the tubing from exposure to light, which may otherwise degrade the light-sensitive medical fluids and/or change their chemical composition, rendering them unsuitable for their intended use.

The aforementioned configuration with the light protection additives and/or colorants incorporated into the intermediate layer is further advantageous in that the inner layer serves as a barrier to prevent any potential harsh chemicals in the light protection additives and/or colorants from leaking into the medical fluid flowing in the tubing lumen, which would otherwise contaminate the medical fluid.

The multi-layer (e.g., three-layer) tubing of the various embodiments described herein may utilize a separate chemicals package comprising light protection additives, which is then incorporated into the carrier resin of the intermediate layer. The tubing may then be extruded either into a single layer, or into multiple layers as shall be described in further detail below. As described herein, the multi-layer (e.g., three-layer) tubing is configured so as to be able to withstand and pass the rigorous testing regulations for light-resistant infusion sets. For example, the Chinese Food and Drug Administration (cFDA) recently published a standard regulation for light-resistant infusion sets for single use infusion in which low and high pH, 65% ethanol and 50% PEG solution is circulated inside of the infusion set at 37 degrees Celsius for 2 hrs. The regulation deems the testing fails if the extracted medium demonstrates darker color than the transparent 65% ethanol and 50% PEG solution. In further cFDA testing regulations, the infusion set is incubated at 60 C for 24 hr and then about a 1 meter length of the outer tubing layer is rubbed with cotton. The regulation deems the testing fails if there is obvious color migration to the outer layer of the tubing where colorant is found on the surface of the cotton used to wipe the tubing. These rigorous testing conditions to test the inner layer chemically and outer layer physically dictate a need for an alternative way to maintain the integrity of the additives in the tubing layers. Accordingly, various embodiments of the present disclosure are directed to providing a three-layer tubing design configuration having an intermediate layer containing the active light-protective additives and/or colorants. The inner layer of the three-layer tubing advantageously acts as a barrier to avoid direct contact of the medical fluid and the light-protectant additives or colorants. The outer layer acts as another barrier to prevent migration of additives from the intermediate layer onto an exterior surface of the three-layer tubing.

A further benefit of tubing of the present disclosure is that the intermediate layer can include one or more of a colorant, UV blocker, radiopaque stripes among other additives. Such additives can be used to design colored tubing and/or light resistant tubing with less concern of such additives leaching to fluid transported by the tubing since the inner layer can prevent migration of such additives.

The three-layer tubing of the present disclosure may be particularly useful with intravenous assemblies and/or infusion pumps for the transport of intravenous fluid to a patient. An assembly of tubing, valves, fittings, and needles that connect a fluid container to a patient intravenously may be referred to as an "intravenous set" or "IV set". An infusion set can include the tubing according to the present disclosure is bond to components of the IV set such as a medical connector, drip chamber, luer, spike, check valve, filters and needleless valve to name a few to accomplish the medical delivery to patients either to be used as gravity sets or controlled by medical pump for programmed medical delivery procedures.

FIG. 1 illustrates a cross-section of a three-layer tubing in accordance with an aspect of the present disclosure. As shown in the FIGURE, tubing, e.g., medical tubing 100 can include an inner layer 10, an outer layer 20 concentrically disposed about and surrounding the inner layer 10, and an intermediate layer 30 interposed between the inner and outer layers 10 and 20. In some embodiments, the outer layer, the inner layer, and the intermediate layer may each be formed from the same base material. For example, the inner layer 10, the outer layer 20, and the intermediate layer 30 may be co-extruded from a same polymeric resin material. The layers 10, 20, and 30 may be co-extruded such that outer layer 20 directly contacts the intermediate layer 30, which in turn, directly contacts the inner layer 10 along the tubing length without a tie layer between the outer layer 20 and the inner layer 10 or between inner layer 10 and intermediate layer 30.

The aforementioned configuration where the inner, outer, and intermediate layers 10, 20, and 30 are formed from the same base resin material advantageously obviates the need for a tie layer, which is conventionally needed to maintain the bond between the multiple layers and prevent delamination of the multiple layers of the tubing. For example, because the same compatible base resin with the same polarity and chemical composition is used in each of the three layers, it is not necessary to have a tie layer in between to keep the layers 10, 20, 30 of the tubing 100 from delaminating.

In accordance with some embodiments, the base resin material may include at least one or a combination of polyvinyl chloride (PVC), styrenic block copolymer (SBC), polyolefin, thermoplastic polyurethane (TPU), polyester, polyether, silicone HCR, EPDM/PP, and any other similar elastomeric materials. Base resin polymeric materials that may be useful for the layers 10, 20, and 30 of the tubing of the present disclosure include, without limitation, medical grade plastic materials such as polyvinyl chloride (PVC), and copolymers thereof and blends of such polymers. In some embodiments, the medical grade plastic materials such as PVC can be made flexible by including varying amounts of plasticizer.

For example, differential in flexibility or hardness can be achieved by including in the polymeric material of inner layer 10 a lower amount of or a different type of plasticizer than outer layer 20 and intermediate layer 30. In some embodiments, the amount of or different type of plasticizer should be sufficient to advantageously achieve a hardness of the outer or intermediate layer to be at least about 5 hardness units smaller than the hardness of inner layer 10. In some embodiments, for example, inner layer 10 may have a lower amount of the same plasticizer than outer layer 20 and intermediate layer 30 to achieve a higher hardness. In some aspects, phthalate esters such as di(2-ethylhexyl) phthalate (DEHP) and adipate esters such as di(2-ethylhexyl) adipate (DEHA) may be used as plasticizers in medical grade PVC tubing.

In accordance with the various embodiments of the present disclosure, the inner, outer, and intermediate layers 10, 20, and 30 may be made of the same base polymeric resin material but the intermediate layer 30 may include a light protection additive. The light protection additive may be dispersed in or otherwise included in the base resin material of the intermediate layer. In some embodiments, the light protection additive may include a pre-determined concentration of ultraviolet (UV) light absorbers. For example, the light protection additive may include a pre-determined concentration of at least one of a benzotriazole, a benzophenone, or a triazine, or a combination thereof. In some embodiments, the light protection additive may include a pre-determined concentration of blue light absorbers.

According to various aspects of the present disclosure, the intermediate layer may further include a colorant, or a mixture of colorants, which appear yellow, amber or brown in color. For example, the colorant or mixture of colorants may include at least one of or a combination of organic dyes, such as Azo dyes, Anthraquinone dyes, Phthalocyanines, or inorganic pigment, such as titanium dioxide, iron oxide, chromium oxide, and other metal oxide and metallic pigments. Such colorants may be used to design a colored intermediate layer with less concern of such colorants leaching to fluid transported by the tubing since the inner layer 10 and the outer layer 20 may act as barriers to prevent migration of the colorants.

In some embodiments, the intermediate layer 30 has a thickness less than the thicknesses of each of the inner and outer layers 10 and 20. For example, in some embodiments the inner and outer layers 10 and 20 may each have a thickness ranging from 0.2 mm to 0.8 mm, such as from 0.4 mm to 0.6 mm. The middle layer may have a thickness that is 10% to 90% of the inner or outer layer such as a thickness less than 0.8 mm, e.g., less than 0.4 mm or less than 0.2 mm. The configuration in which the middle layer has a thickness less than 0.8 to 0.2 mm may be advantageous in increasing the light blocking or protecting capabilities of the intermediate layer 30 given a particular wavelength of the light incident on the tubing 100. For example, a thinner intermediate layer may provide a more desirable transmittance ratio of the light incident on the tubing 100 particular wavelength of the light. In some embodiments a combined thickness of the inner, outer, and intermediate layers may be less than or equal to 0.8 mm, with the intermediate layer having a thickness less than the thicknesses of each of the inner and outer layers 10 and 20. Further, in some embodiments, tubing of the present discloser can have an inner diameter for flow of fluid therethrough ranging from about 1.5 mm to about 6 mm, e.g., from 2 mm to 4 mm.

Accordingly, incorporating the aforementioned light protection additives or colorants into the intermediate layer 30 of the tubing may advantageously provide at least the minimum requisite light protection capability in the range of 250 to 450 nm with a minimum 90% blockage, or minimum 10% transmittance. Accordingly, light-sensitive medical fluids flowing in the tubing 100 may be protected from harmful exposure to the light, which may otherwise degrade the light-sensitive medical fluids and/or change their chemical composition, such that they may become harmful to the patient if they enter the patient bloodstream.

In some embodiments, the intermediate layer may further include a radiopaque material. The radiopaque material may advantageously function as an x-ray-sensitive tracking mark to identify the tubing's location in human body.

In some embodiments, the intermediate layer may further include a stripe identifier. In some aspects, patients have multiple tubings attached to their bodies in different locations. For example, the patient may have one or more of intravenous (IV) tubing, subcutaneous tubing, epidural tubing, feeding tubing, arterial lines or tubing, plural drainage lines or tubing. In these instances, the stripe identifier may advantageously color code the tubing to prevent the wrong medication from going in the wrong location of the body. The color codes help to make sure the medication or other medical fluids are easily identified and associated with the final location of the respective tubings. Accordingly, sever adverse effects associated with the wrong medication being delivered to the wrong location on the body may be avoided.

According to various embodiments of the present disclosure, a method of forming a multi-layer tubing 100 may include co-extruding a base polymeric resin material into an inner layer 10, an outer layer 20, and an intermediate layer 30 of the multi-layer tubing. The layers 10, 20, and 30 may be co-extruded such that outer layer 20 directly contacts the intermediate layer 30, which in turn, directly contacts the inner layer 10 along the tubing length without a tie layer between the outer layer 20 and the inner layer 10 or between inner layer 10 and intermediate layer 30. The method of forming the multi-layer tubing may further include incorporating the light protection additive having a predetermined concentration into the intermediate layer 30 prior to the co-extruding. In some embodiments, the light protection additive may include one or more of ultraviolet (UV) or blue light absorbers, a colorant, or a mixture of colorants which appear yellow, amber or brown in color, a radiopaque material, or a stripe identifier.

Accordingly, the various embodiments of the present disclosure incorporate active additives in the intermediate layer as opposed to the inner or outer layers in order to minimize and avoid tubing testing failure where colorant migrates to the outer surface of the tubing, as described above. Further advantageously, the various embodiments of the present disclosure incorporate active additives in the intermediate layer as opposed to the inner or outer layers in order to reduce the potential risks associated with the additives migrating into the tubing lumen and causing hazardous contamination with the fluid being administered. The contamination may become more serious where the fluid is introduced into the body, and resulting contamination of the blood may occur.

Further advantageously, since the inner, outer, and intermediate layers are made of the same polymeric base material, the layers are more readily compatible and can more readily fuse together thereby avoiding or minimizing the need to include an adhesive or tie layer between the outer and inner, and, intermediate layers greatly simplifying and reducing the cost of the extrusion process for making such tubing.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A tubing comprising an inner layer, an outer layer concentrically disposed about and surrounding the inner layer, and an intermediate layer interposed between the inner and outer layers,
    wherein the intermediate layer comprises a light protection additive included therein, the intermediate layer providing protection from light between 250 nm to 450 nm with a minimum of 90 percent blockage, and the inner layer and the outer layer being barriers to prevent migration of the light protection additive from the intermediate layer,
    wherein the intermediate layer has a thickness less than the thickness of at least one of the inner and outer layers,
    wherein the inner layer, the outer layer, and the intermediate layer are formed from a same base resin material,
    wherein a hardness of each of the outer layer and the intermediate layer is at least 5 hardness units less than the hardness of the inner layer.

2. The tubing of claim 1, wherein the light protection additive is included in the base resin material of the intermediate layer and comprises a pre-determined concentration of at least one of ultraviolet (UV) or blue light absorbers.

3. The tubing of claim 1, wherein the base resin material comprises a plasticized polyvinyl chloride.

4. The tubing of claim 1, wherein the base resin material comprises silicone heat cured rubber.

5. The tubing of claim 1, wherein the intermediate layer further comprises a colorant, or a mixture of colorants, which appears yellow, amber or brown in color.

6. The tubing of claim 5, wherein the colorant or the mixture of colorants comprise Azo dyes, Anthraquinone dyes, Phthalocyanines, Iron oxide, Chromium Oxide, and other metal oxide and metallic pigments.

7. The tubing of claim 1, wherein the inner layer and the outer layer are co-extruded in direct contact with the intermediate layer along a length of the tubing.

8. The tubing of claim 1, wherein the light protection additive comprises a UV light absorber including at least one of a benzotriazole, a benzophenone, or a triazine, or combinations thereof.

9. The tubing of claim 1, wherein the intermediate layer further comprises at least one of a stripe identifier or a radiopaque material.

10. The tubing of claim 5, wherein the colorant or the mixture of colorants comprise Azo dyes.

11. The tubing of claim 5, wherein the colorant or the mixture of colorants comprise Anthraquinone dyes.

12. A method of forming a multi-layer tubing, comprising:
co-extruding a base polymeric resin material into the multi-layer tubing comprising an inner layer, an outer layer concentrically disposed about and surrounding the inner layer, and an intermediate layer interposed between the inner and outer layers of the multi-layer tubing,
wherein the intermediate layer comprises a light protection additive included therein, the intermediate layer providing protection from light between 250 nm to 450 nm with a minimum of 90 percent blockage, and the inner layer and the outer layer being barriers to prevent migration of the light protection additive from the intermediate layer,
wherein the intermediate layer is co-extruded to a thickness less than that of at least one of the inner and outer layers,
wherein the inner layer, the outer layer, and the intermediate layer are formed from the same base polymeric resin material, and
wherein a hardness of each of the outer layer and the intermediate layer is at least 5 hardness units less than the hardness of the inner layer.

13. The method of claim 12, wherein the light protection additive comprises a pre-determined concentration of at least one of ultraviolet (UV) and blue light absorbers.

14. The method of claim 12, wherein the intermediate layer further comprises a pre-determined concentration of a colorant, or a mixture of colorants, which causes the intermediate layer to appear yellow, amber or brown in color.

15. The method of claim 14, wherein the colorant or the mixture of colorants comprise Iron oxide.

16. The method of claim 12, wherein the intermediate layer is extruded to a thickness less than 0.8 mm.

17. The method of claim 12, wherein the base polymeric resin material comprises thermoplastic polyurethane (TPU).

18. The method of claim 12, wherein the intermediate layer further comprises at least one of a stripe identifier or a radiopaque material.

* * * * *